United States Patent [19]

Yamazaki

[11] Patent Number: 4,794,933
[45] Date of Patent: Jan. 3, 1989

[54] ULTRASONIC BLOOD STREAM OBSERVING APPARATUS

[75] Inventor: Nobuo Yamazaki, Otawara, Japan

[73] Assignee: Kabushiki Kaisha Toshiba, Kanagawa, Japan

[21] Appl. No.: 97,181

[22] Filed: Sep. 16, 1987

[30] Foreign Application Priority Data

Sep. 29, 1986 [JP] Japan .................. 61-230607

[51] Int. Cl.$^4$ .............................................. A61B 10/00
[52] U.S. Cl. ............................................. 128/661.09
[58] Field of Search .................. 128/663, 660; 73/631, 73/861.25

[56] References Cited

U.S. PATENT DOCUMENTS

| | | | |
|---|---|---|---|
| 4,169,385 | 9/1979 | Kellogg et al. | 128/660 |
| 4,485,821 | 12/1984 | Iinuma | 128/663 |
| 4,534,357 | 8/1985 | Powers | 128/663 |
| 4,542,657 | 9/1985 | Barber et al. | 73/861 |
| 4,545,251 | 10/1985 | Uchida et al. | 73/631 |
| 4,573,477 | 3/1986 | Namekawa et al. | 128/663 |
| 4,653,000 | 3/1987 | Matsumoto | 128/660 |
| 4,660,565 | 4/1987 | Shirasaka | 128/663 |

FOREIGN PATENT DOCUMENTS 2736541 2/1979 Fed. Rep. of Germany ...... 128/706

OTHER PUBLICATIONS

Fundamentals Handbook of Electrical and Computer Eng. 1983, Wiley-Interscience pp. 204-205, Author Chang.

Primary Examiner—Francis J. Jaworski
Assistant Examiner—George Manuel
Attorney, Agent, or Firm—Finnegan, Henderson, Farabow, Garrett, & Dunner

[57] ABSTRACT

An ultrasonic blood stream observing apparatus based on a pulse Doppler method utilizing as a transmission, a high frequency pulse signal. The frequency $f_{PRF}$ of a transmission pulse repetition signal and the frequency $f_R$ of a reference signal used for demodulating a Doppler component of an observed signal, are synchronized to each other. The frequency $f_{PRF}$ is a harmonic frequency. The output of an oscillator is frequency-divided to produce the transmission pulse repetition signal. A frequency multiplier generates an output signal used as the reference signal, synchronized to the transmission pulse repetition signal. The frequency multiplier frequency multiplies by n its input signal obtained directly or indirectly from the oscillator.

8 Claims, 6 Drawing Sheets

ULTRASONIC BLOOD STREAM OBSERVING APPARATUS

BACKGROUND OF THE INVENTION

The present invention relates to an apparatus for obtaining the information on a blood stream within a body under examination at a certain depth below the skin surface by utilizing ultrasonic Doppler imaging, and more particularly to such an ultrasonic blood stream observing apparatus capable of obtaining highly accurate blood stream information at a desired depth within a body being examined.

Ultrasonic Doppler imaging is based on the principle that when an ultrasonic wave is reflected by a moving object, the reflection is subjected to a frequency shift proportional to the speed of movement of the moving body. More specifically, ultrasonic rate pulses or a continuous ultrasonic wave is transmitted into a living body, and the echo has a frequency shift due to its phase change according to the Doppler effect. The frequency shift is utilized to obtain the information on movement of the moving object at a depth where the echo is produced. Such ulstrasonic Doppler imaging is effective in gaining blood stream information which indicates various blood stream conditions in a certain position within a living body, such for example as the direction of the blood stream, whether the blood stream is disturbed or smooth, the pattern of the blood stream, and the absolute value of the speed of flow of the blood stream.

Figure 9:
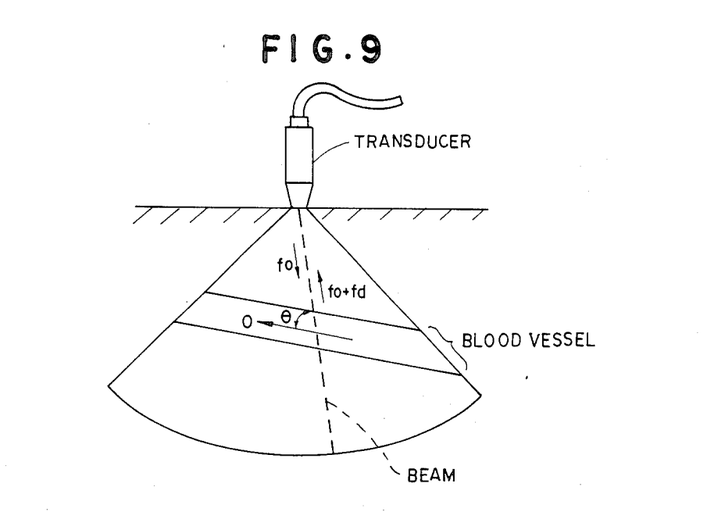
FIG. 9 is a view illustrative of the principles of blood stream observation.

FIG. 9 of the accompanying drawings shows the manner in which ultrasonic Doppler imaging is carried out. When an ultrasonic beam having a frequency $f_0$ is transmitted from a transducer into a living body under examination at an incident angle $\theta$ with respect to a blood stream in a blood vessel, the frequency $f_0$ is shifted upon being reflected from the moving object or blood stream which flows at a speed v. Assuming that the shifted frequency, which is the frequency of a received signal, is expressed by $f_0'$, the frequencies $f_0$, $f_0'$ have the following relationship (1):

$$f_0' = \frac{1 + \frac{v \cos \theta}{C}}{1 - \frac{v \cos \theta}{C}} \cdot f_0 \qquad (1)$$

where C is the speed of travel of the ultrasonic beam in the living body.

Since the speed of sound within the living body is sufficiently higher than the blood stream speed v, the frequency shift fd ($=f_0'-f_0$) can approximately be given by the following equation (2):

$$fd = \frac{2v \cos \theta}{C} \cdot f_0 \qquad (2)$$

Ordinary ultrasonic blood stream observing apparatus display the above Doppler frequency shift fd.

In the pulsed Doppler imaging process in which high-frequency pulses are employed as a transmitted signal, there are transmitted spectra present at increments of a pulse repetition frequency (rate pulse) $f_{PRF}$ from the central frequency $f_0$. Therefore, a signal is received with respect to each of the spectra, and the Doppler signal at $f_0+nf_{PRF}$ can be expressed by the following equation (3) which is derived by modifying the above equation (2):

$$fdn = \frac{2v \cos \theta}{C} (f_0 + nf_{PRF}) \qquad (3)$$

where n is an integer.

According to the pulsed Doppler imaging process, the Doppler component fdn in each $f_0+nf_{PRF}$ can be selected as desired within an allowable range of S/N ratio. In general, which Doppler component is to be extracted can be determined by a reference frequency $f_R$ used when demodulating the Doppler component from a high-frequency range into an audible range. The obtained Doppler signal is expressed by the equation (4):

$$fd = \frac{2v \cos \theta}{C} \cdot f_R \qquad (4)$$

The reference frequency $f_R$ should preferably be set to a frequency with the highest S/N ratio in the received spectrum. It is necessary that the pulse repetition frequency $f_{PRF}$ and the reference frequency $f_R$ be completely in synchronism with each other since if the pulse repetition frequency $f_{PRF}$ and the reference frequency $f_R$ were brought out of phase in time, such an out-of-phase condition would be detected as a Doppler frequency shift resulting in unwanted noise.

Figure 10:
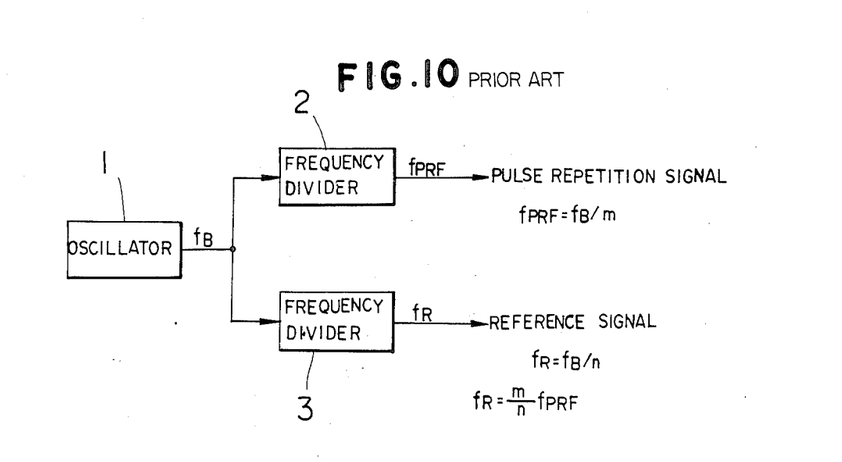
FIG. 10 is a block diagram of a conventional arrangement.

The pulse repetition frequency $f_{PRF}$ and the reference frequency $f_R$ have heretofore been generated as shown in FIG. 10 of the accompanying drawings. An oscillator 1 produces a reference clock signal $f_B$, which is frequency-divided at 1/m (m is an integer) into a pulse repetition frequency $f_{PRF}$ ($=f_B/m$) by a frequency divider 2. The reference clock signal $f_B$ from the oscillator 1 is also frequency-divided at 1/n (n is an integer) into a reference frequency $f_R$ ($=f_B/n$) by a frequency divider 3.

As described above, the reference frequency $f_R$ should preferably be set to a frequency with the highest S/N ratio in the received spectrum. Because the reference frequency $f_R$ is produced by frequency-dividing the reference clock signal $f_B$ with the frequency divider 3 as shown in FIG. 10, the reference clock signal $f_B$ should be of a high frequency in order to vary the reference frequency $f_R$ in small steps, with the results that the circuit is large and noise is increased.

In order to achieve full synchronism between the pulse repetition frequency $f_{PRF}$ and the reference frequency $f_R$, the following relationship must be met:

$f_R/f_{PRF} = m/n =$ integer

This imposes limitations on the selection of m, n, i.e., the pulse repetition frequency $f_{PRF}$ and the reference frequency $f_R$.

Inasmuch as the pulse repetition frequency $f_{PRF}$ and the reference frequency $f_R$ have been generated by frequency-dividing the reference clock signal in the conventional ultrasonic blood stream observing apparatus, the reference frequency $f_R$ cannot be set to a desired value. Moreover, it has been difficult to bring the pulse repetition frequency $f_{PRF}$ and the reference frequency $f_R$ into synchronism with each other. As a consequence, blood stream observations at desired depths cannot be effected with high accuracy.

SUMMARY OF THE INVENTION

It is a first object of the present invention to provide an ultrasonic blood stream observing apparatus which is capable of obtaining a desired reference frequency $f_R$ without increasing the frequency of a reference clock signal $f_B$ and of easily synchronizing the reference frequency $f_R$ and a pulse repetition frequency $f_{PRF}$.

A second object of the present invention is to provide an ultrasonic blood stream observing apparatus which can be adjusted to obtain a reference frequency having a highest S/N ratio for thereby allowing blood stream observations to be made at desired depths with high accuracy.

According to the present invention, the aforesaid first object can be accomplished by an ultrasonic blood stream observing apparatus comprising: a transducer for transmitting an ultrasonic wave into and receiving an ultrasonic wave from a body under examination; reference signal generating means including an oscillator for generating an output signal of a prescribed frequency, a frequency divider for frequency-dividing the output signal from the oscillator, and a multiplier for generating a reference signal in synchronism with the output signal from the frequency divider or an output signal from the oscillator, the reference signal having a frequency which is a multiple of the frequency of the output signal from the frequency divider or the oscillator; demodulating means for demodulating a Doppler component in a high-frequency range including a scattered ultrasonic wave in the signal received by the transducer, with the reference signal from the multiplier; and frequency analyzing means for analyzing the frequency of an output signal from the demodulating means to obtain blood stream information at a prescribed depth in the body under examination.

According to the present invention, the second object can be accomplished by an ultrasonic blood stream observing apparatus comprising: a transducer for transmitting an ultrasonic wave into and receiving an ultrasonic wave from a body under examination; reference signal generating means including an oscillator for generating an output signal of a prescribed frequency, a frequency divider for frequency-dividing the output signal from the oscillator, and a multiplier for generating a reference signal in synchronism with the output signal from the frequency divider or an output signal from the oscillator, the reference signal having a frequency which is a multiple of the frequency of the output signal from the frequency divider or the oscillator; demodulating means for demodulating a Doppler component in a high-frequency range including a scattered ultrasonic wave in the signal received by the transducer, with the reference signal from the multiplier; frequency analyzing means for analyzing the frequency of an output signal from the demodulating means to obtain blood stream information at a prescribed depth in the body under examination; and a reference signal correcting circuit for integrating the spectral intensity of the analyzed output signal and feeding the integral back to the reference signal generating means.

The above and other objects, features and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
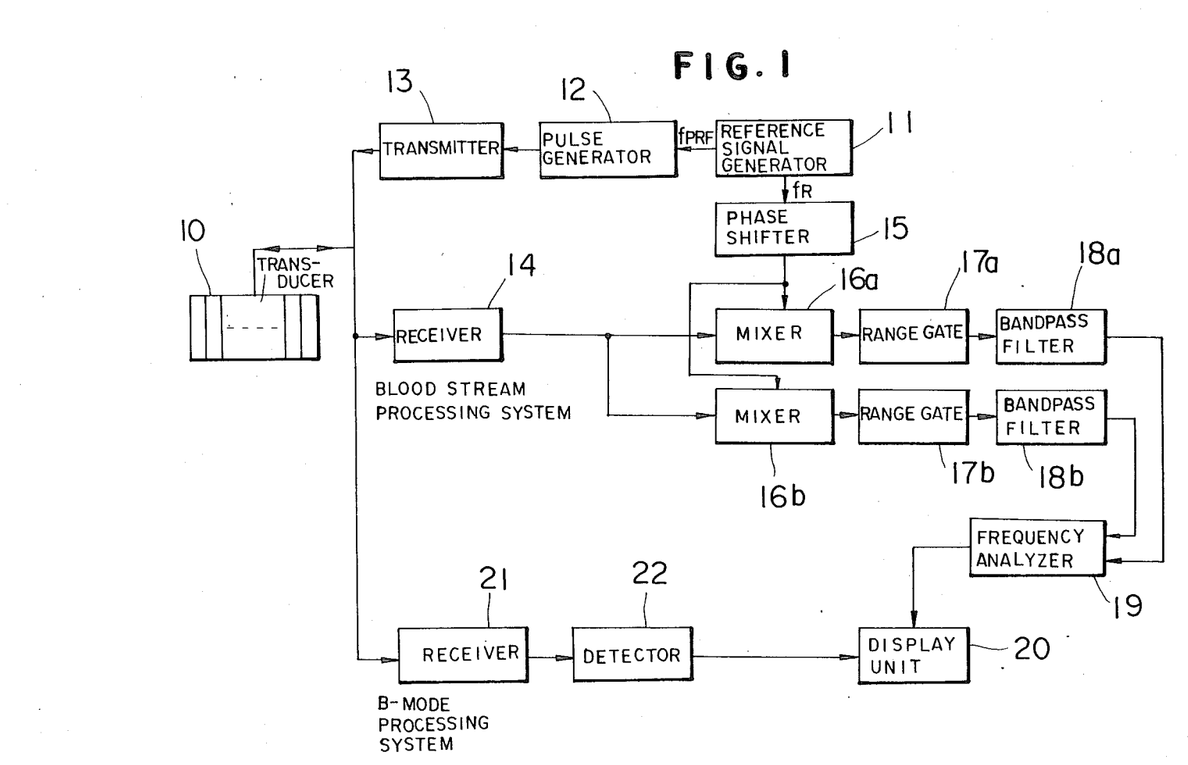
FIG. 1 is a block diagram of an ultrasonic blood stream observing apparatus according to a first embodiment of the present invention.

As shown in FIG. 1, an ultrasonic blood stream observing apparatus according to a first embodiment of the present invention includes an electronic scanning ultrasonic transducer 10 comprising an array of ultrasonic oscillators for generating an ultrasonic wave in response to a pulse repetition frequency $f_{PRF}$ produced by a reference signal generator 11 and applied through a pulse generator 12 and a transmitter 13. The apparatus also includes an ultrasonic receiving section composed of a blood stream processing system and a B-mode processing system. The B-mode processing system has a receiver 21 and a detector 22 which processes a received signal and applies the processed signal to a display unit 20.

The blood stream processing system includes a receiver 14 for applying a received signal to two mixers 16a, 16b. Signals from the mixers 16a, 16b are processed by respective range gates 17a, 17b and respective bandpass filters 18a, 18b the output signals from which are analyzed by a frequency analyzer 19 that sends an output signal to the display unit 20 for display. The reference signal generator 11 produces a reference signal $f_R$ which is converted by a phase shifter 15 into two signals that are 90° out of phase with each other and supplied to the respective mixers 16a, 16b. The phase shifter 15 produces the two 90°-out-of-phase signals in order to separate a blood stream flowing toward the transducer 10 from a blood stream flowing away from the transducer 10. More specifically, the phase shifter 15 multiplies the frequency of the reference signal $f_R$ by four ($4f_R$) and then divides the multiplied signal by four thereby to generate the two signals that are out of phase with each other.

Certain blocks in FIG. 1 which constitute a central part of the present invention will be described below.

Figure 3:
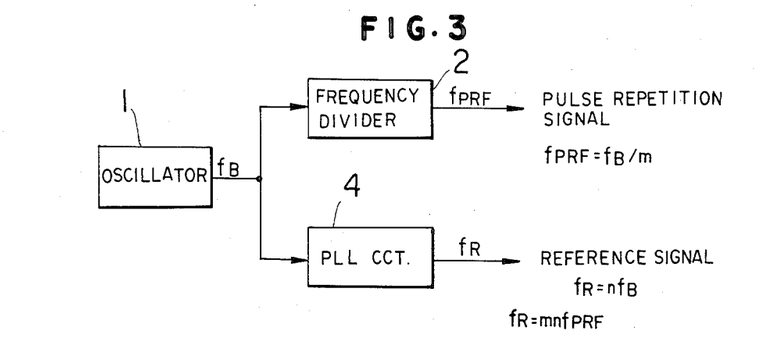
FIG. 3 is a detailed block diagram of a reference signal generator in the apparatus according to the above embodiments.

As shown in FIG. 3, the reference signal generator 11 comprises an oscillator 1 which produces a reference clock signal $f_B$, a frequency divider 2 for frequency-dividing the reference clock signal $f_B$ at $1/m$ into a pulse repetition frequency $f_{PRF}$ ($=f_B/m$), and a phase-locked loop (PLL) circuit 4, which is one example of a multiplier, responsive to the reference clock signal $f_B$ from the oscillator 1 for generating a reference frequency $f_R$ ($=nf_B$, $=mnf_{PRF}$) in synchronism with the reference frequency $f_B$.

Figure 4:
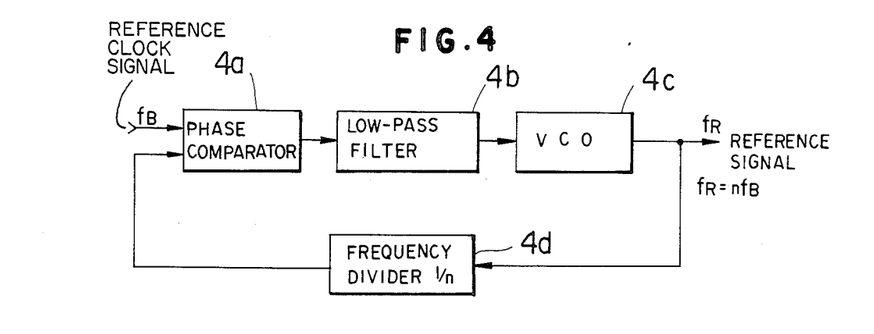
FIG. 4 is a detailed block diagram of a phase-locked loop (PLL) circuit in the reference signal generator shown FIG. 3.

As illustrated in FIG. 4, the phase-locked loop circuit 4 comprises a phase comparator 4a, a low-pass filter 4b, a voltage-controlled oscillator 4c, and a frequency divider 4d. The phase comparator 4a compares the phase of the frequency $f_B$ of the reference clock signal applied as an input signal and the phase of the frequency of the output signal applied from the frequency divider 4d which has a frequency-dividing ratio 1/n, generates a voltage proportional to the phase error, and applies the generated voltage via the low-pass filter 4b to the voltage-controlled oscillator 4c as a control input signal. The output frequency or reference frequency $f_R$ ($=nf_B$, $=mnf_{PRF}$) from the voltage-controlled oscillator 4c is varied so as to reduce the frequency difference and phase difference between the reference clock signal and the output signal from the voltage-controlled oscillator 4c. The reference frequency $f_R$ can be varied in steps ($f_R=nf_B$) by varying the frequency-dividing ratio 1/n of the frequency divider 4d.

With the arrangement shown in FIGS. 3 and 4, it is possible to reduce or make finer the steps for varying the reference frequency $f_R$ by lowering the frequency $f_B$ of the reference clock signal.

Operation of the above ultrasonic blood stream observing apparatus will be described below.

When a pulse repetition frequency $f_{PRF}$ ($=f_B/m$) is applied from the reference signal generator 11 to the pulse generator 12, the pulse generator 12 frequency-divides the applied frequency to produce a rate signal for repeatedly transmitting an ultrasonic pulse. The rate signal is supplied to the transmitter 13 for energizing the ultrasonic oscillators of the transducer 10 under delay control thereby to apply ultrasonic pulses to a living body (not shown) under examination.

An ultrasonic wav reflected from the living body, i.e., a region where a blood stream is to be observed, is received by the ultrasonic oscillators of the transducer 10, amplified by the receiver 14, and applied as a received signal to the mixers 16a, 16b. The mixers 16a, 16b, which are supplied with the respective reference signals, 90° out of phase with each other, from the phase shifter 15, mix the received signal with the reference signals, respectively, to detect the phase of the received signal. The differences between the received signal and the reference signals are extracted by the mixers 16a, 16b and applied to the respective range gates 17a, 17b. With the reference signals applied respectively to the mixers 16a, 16b being 90° out of phase with each other, one of the mixers 16a, 16b extracts an advanced frequency shift whereas the other mixer extracts a delayed frequency shift.

The range gates 17a, 17b supplied with the extracted and phase-detected signals select signals from respective time intervals or gates in order to extract signals corresponding to the region to be observed. Thereafter, the signals selected from the range gates 17a, 17b are passed through the respective bandpass filters 18a, 18b for removing large echoes due to walls of nearby organs and also for removing harmonics that have been created by the range gates 17a, 17b. The signals are then delivered from the bandpass filters 18a, 18b to the frequency analyzer 19. The frequency analyzer 19 analyzes the frequencies of the applied signals to determine a distribution of frequency shifts of the echoes within the range gates 17a, 17b. The results are sent to the display unit 20 such as a monitor display unit which then displays obtained blood stream information.

In the B-mode processing system, the received signal is first applied to the receiver 21 which produces an output signal that is detected by the detector 22 having logarithmic characteristics. The detector 22 produces sectional image information which is applied to the display unit 20 on which the sectional image information is displayed together with the blood stream information.

With the first embodiment, as described above, the reference frequency $f_R$ is generated by a frequency synthesizer by applying the reference clock signal to the phase-locked loop circuit. Therefore, the reference frequency $f_R$ can be set to a desired value even if the output frequency of the oscillator has a low setting. The reference frequency adjustment can be effected by varying the frequency-dividing ratio 1/n of the frequency divider of the PLL circuit.

Inasmuch as the reference frequency $f_R$ and the pulse repetition frequency $f_{PRF}$ can easily be brought into synchronism with each other, the reference frequency $f_R$ can be set to a value with highest S/N ratio, with the result that highly accurate blood stream observations can be made at desired depths in the body being examined.

Figure 2:
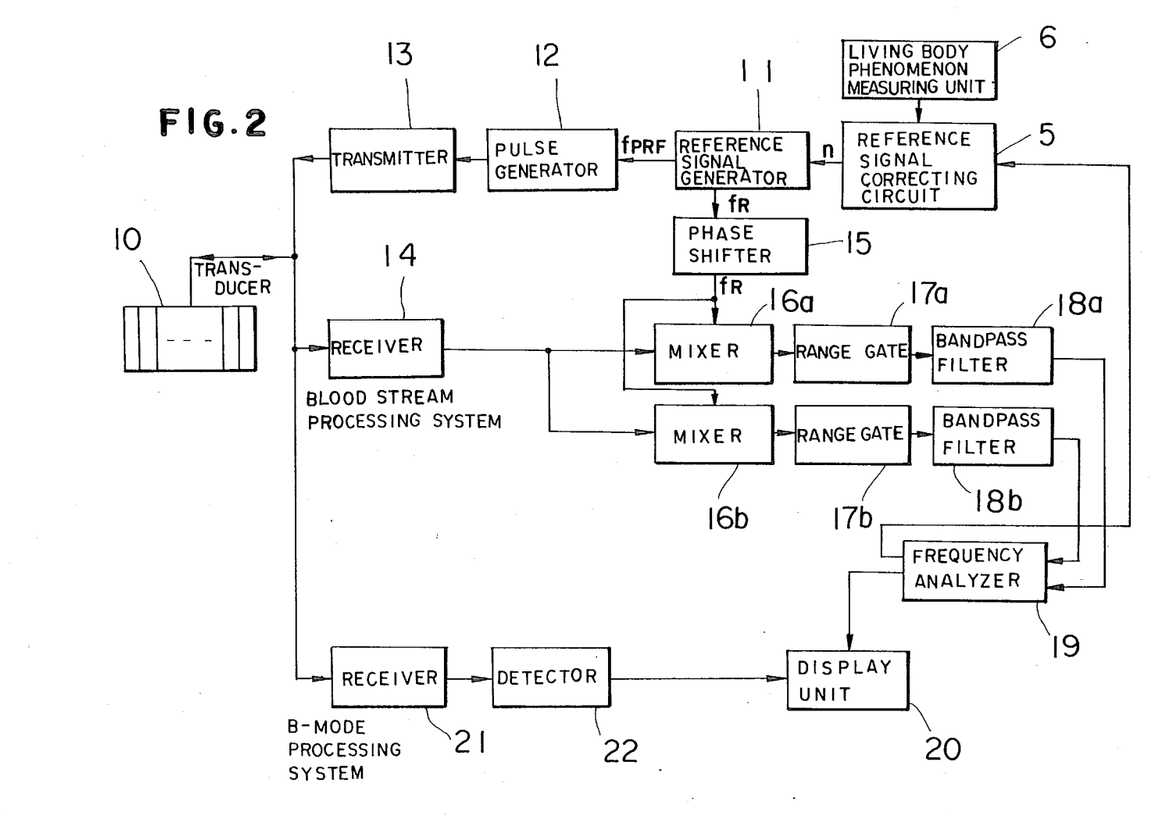
FIG. 2 is a block diagram of an ultrasonic blood stream observing apparatus according to a second embodiment of the present invention.

A second embodiment of the present invention will be described with reference to FIG. 2.

The second embodiment differs from the first embodiment in that the reference signal generator 11 is connected to a reference signal correcting circuit 5 which produces a signal n for correcting the reference signal $f_R$ based on the output signal from the frequency analyzer 19. The reference signal correcting circuit 5 effects an arithmetic operation in synchronism with a synchronizing signal which is supplied from a living body phenomenon measuring unit 6 based on a pulsation signal.

Figure 6:
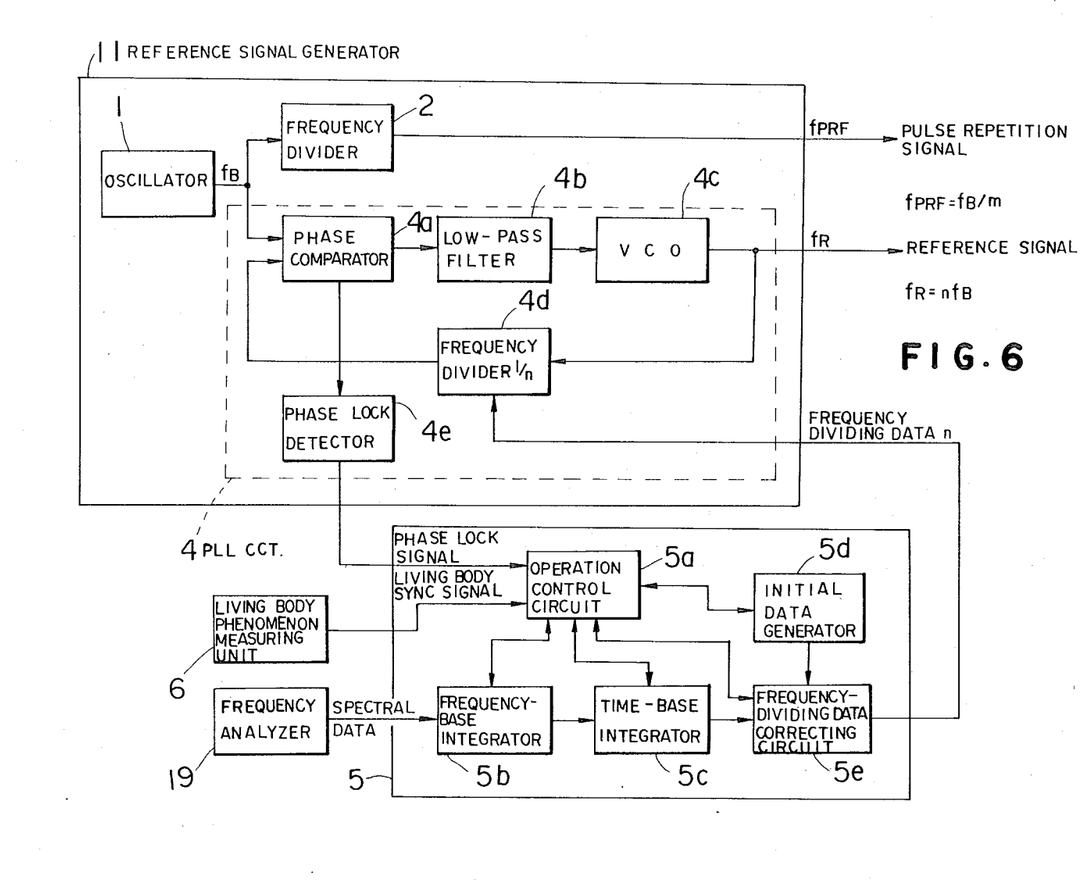
FIG. 6 is a block diagram showing, in greater detail, a reference signal correcting circuit and a PLL circuit in the apparatus according to the second embodiment.

The reference signal correcting circuit 5 as it is connected to the reference signal generator 11 will be described with reference to FIG. 6.

The reference signal correcting circuit 5 comprises a operation control circuit 5a synchronized by a synchronizing signal from the living body phenomenon measuring unit 6, a frequency-base integrator 5b for integrating spectral data from the frequency analyzer 19 with respect to a frequency base, a time-base integrator 5c for integrating spectral data from the frequency analyzer 19 with respect to a time base, an initial data generator 5d, and a frequency-dividing data correcting circuit 5e for correcting frequency-dividing data with initial data from the initial data generator 5d and integrals from the integrators 5b, 5c. The elements 5a through 5e of the reference signal correcting circuit 5 are controlled by control signals from the control circuit 5a. The results of the integrating operations and data items are stored in a memory in the control circuit 5a.

An output signal n from the frequency-dividing data correcting circuit 5e is applied to a frequency-dividing ratio control terminal of the frequency divider 4d in the PLL circuit 4.

The PLL circuit 4 and the reference signal correcting circuit 5 are operatively associated with each other by a phase lock detector 4e which is provided in the PLL circuit 4 for applying an output signal to the operation control circuit 5a.

Operation of the second embodiment is essentially the same as that of the first embodiment, except for correcting action of the reference signal correcting circuit 5.

Figures 7, 8:
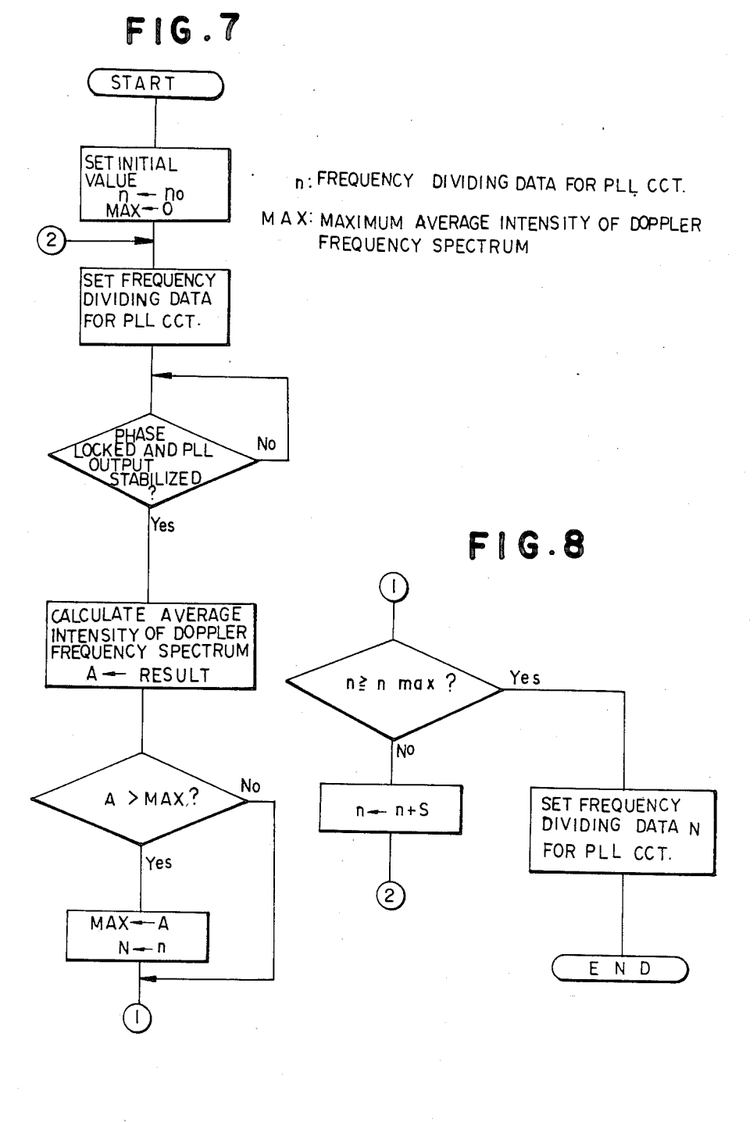
FIGS. 7 and 8 are a flowchart of an operation sequence of the apparatus according to the second embodiment.

The corrective action of the reference signal correcting circuit 5 will be described with reference to FIGS. 7 and 8.

The reference signal correcting circuit 5 is started by the operator through an operation unit (not shown). The initial data generator 5d of the correcting circuit 5 generates an initial value $n_0$ of the frequency-dividing data n for producing a reference signal corresponding to the transmission frequency of the ultrasonic transducer 10. The initial value $n_0$ is applied via the frequency-dividing data correcting circuit 5e to the 1/n frequency divider 4d of the PLL circuit 4.

At this time, the PLL circuit 4 operates so that the reference signal $f_R = n_0 f_B$, and the operation control circuit 5a of the correcting circuit 5 is provided with a phase lock signal indicating that the phase of the phase comparator 4a is locked and stable oscillation is effected at $f_R$.

In response to this phase lock signal applied to the control circuit 5a, the correcting circuit 5 starts carrying out an initial operation. The corrective operations are controlled by the phase lock signal in order to inhibit any corrective operations during transitions until the oscillation frequency that has been varied by varying the frequency-dividing ratio 1/n in the PLL circuit is stabilized.

The correcting circuit 5 integrates spectral data of the Doppler signal obtained by the frequency analyzer 19 with respect to the frequency and time bases. The values thus calculated, i.e., integrals, are indicative of the average intensities of the Doppler signal with respect to the frequency and time bases. These values are stored in the correcting circuit as average intensities with respect to the frequency-dividing ratio $1/n_0$.

The frequency-dividing ratio of the PLL circuit is varied bit by bit with respect to the initial data value $n_0$ and given to the frequency divider for thereby varying the frequency of the reference signal $f_R$ in small increments. The above integrating operations are repeated each time it is recognized that the oscillation frequency is stabilized by way of the phase lock signal. While adjusting the frequency of the reference signal in small increments in the above manner, the average intensities of the Doppler signal are calculated, and the frequency of the reference signal at which the average intensities are highest is determined. The frequency-dividing ratio 1/n at this time is set again by the correcting circuit 5, whereupon the automatic ratio setting process is stopped.

Through the above operation of the correcting circuit, the frequency of the reference signal can automatically be set to the frequency at which a Doppler signal with a highest S/N ratio can be obtained.

The accuracy of calculations of the average intensities can be increased by effecting the above integrating operations in synchronism with a living body signal such as an electrocardiogram, for example.

With the embodiments of the present invention, the frequency $f_R$ of the reference signal can be set to a desired value by varying the frequency-dividing ratio of the frequency divider 4d of the PLL circuit 4. Since the frequency divider 2 and the PLL circuit 4 are supplied with the same input signal, the frequency $f_R$ of the reference signal can be synchronized with the pulse repetition frequency $f_{PRF}$, and can be set to a frequency of the reception spectrum at which the S/N ratio is highest. As the region to be observed in a living body under examination becomes deeper, the frequency $f_R$ of the reference signal may be lowered in view of the attenuation characteristics of the high-frequency components of an ultrasonic wave in the living body, so that highly accurate blood stream information can be observed at a desired depth in the living body.

Figure 5:
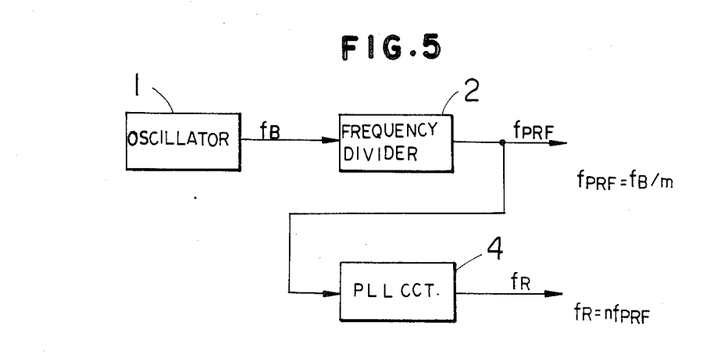
FIG. 5 is a detailed block diagram of a reference signal generator according to another embodiment.

As shown in FIG. 5, the reference signal generator 11 may be arranged such that the reference clock signal $f_B$ from the oscillator 1 is applied to the frequency divider 2 which frequency-divides the reference clock signal $f_B$ at 1/m to produce a pulse repetition frequency $f_{PRF}$ ($=f_B/m$) that is applied as an input signal to the phase-locked loop circuit 4. This arrangement ensures complete synchronism between the pulse repetition frequency $f_{PRF}$ and the frequency $f_R$ of the reference signal.

The PLL circuit may be replaced with any of various other known multipliers.

Although certain preferred embodiments have been shown and described, it should be understood that many changes and modifications may be made therein without departing from the scope of the appended claims.

What is claimed is:

1. An ultrasonic blood flow stream observing apparatus comprising:
    a transducer for transmitting and receiving an ultrasonic wave to and from a body under examination;
    oscillator means for generating a predetemined frequency signal;
    means for frequency dividing said predetermined frequency signal for converting the output of said oscillator means into a transmission pulse repetition signal for driving said transducer;
    means coupled to said oscillator means for frequency multiplying said predetermined frequency signal by a selectable integer value n for converting said predetermined frequency signal into a reference signal synchronized to said transmission pulse repetition signal and variable with respect to said pulse repetition signal for a different selected n
    phase difference detecting means, coupled to receive a signal representative of said received ultrasonic wave from said transducer and to receive said reference signal, for extracting a phase difference between said signal from said transducer and said reference frequency signal and to provide an output thereof; and
    frequency analyzer means for frequency-analyzing the output of said phase difference detecting means to produce a frequency spectrum representative of said blood steam flow.

2. An ultrasonic blood steam observing apparatus according to claim 1, wherein said frequency multiplier means is a phase-locked loop circuit.

3. An ultrasonic blood stream observing apparatus according to claim 1, wherein said predetermined frequency signal is directly applied to said frequency multiplier means as said input signal.

4. An ultrasonic blood stream observing apparatus according to claim 1 wherein said input signal of said frequency multiplier means is obtained via said frequency divider means, said transmission pulse repetition signal being said input signal.

5. An ultrasonic blood flow stream observing apparatus comprising:

a transducer for transmitting and receiving an ultrasonic wave to and from a body under examination;

oscillator means for generating a predetermined frequency signal;

means for frequency dividing said predetermined frequency signal for converting the output of said oscillator means into a transmission pulse repetition signal for driving said transducer;

means coupled to said oscillator means for frequency multiplying said predetermined frequency signal by a selectable integer value n for converting said predetermined frequency signal into a reference signal synchronized to said transmission pulse repetition signal and variable with respect to said pulse repetition signal for a different selected n by said frequency multiplier means having a multiplication factor control terminal, a signal at which controls the valve of n;

phase difference detection means, coupled to receive a signal representative of said received ultrasonic wave from said transducer and to receive said reference signal, for extracting a phase difference between said signal from said transducer and said reference frequency signal and to provide an output the frequency analyzer means for frequency-analyzing the output of said phase difference detection means to produce a frequency spectrum representative of said blood stream flow; and a reference frequency signal correcting circuit for integrating the frequency spectral intensity of said frequency-analyzed signal and feeding data responsive to the resultant integral back to said frequency multiplication factor control terminal of said frequency multiplier means to control the valve of n.

6. An ultrasonic blood stream observing apparatus according to claim 5, wherein said frequency multiplier means comprises a phase-locked loop circuit.

7. An ultrasonic blood stream observing apparatus according to claim 5, wherein said reference signal correcting circuit comprises means for integrating the frequency spectral intensity with respect to frequency and time bases and corresponding to a maximum integral thereof.

8. An ultrasonic blood stream observing apparatus according to claim 5, wherein said reference frequency signal correcting circuit comprises means for integrating the frequency spectral intensity in synchronism with a pulsation signal obtained from said body.

* * * * *

UNITED STATES PATENT AND TRADEMARK OFFICE
CERTIFICATE OF CORRECTION

PATENT NO. : 4,794,933

DATED : January 03, 1989

INVENTOR(S) : Nobuo Yamazaki

It is certified that error appears in the above-identified patent and that said Letters Patent is hereby corrected as shown below:

Claim 1, column 8, line 27, change "blood flow stream observing" to --blood stream flow observing --.

Claim 1, column 8, line 43, add --;-- after "n".

Claim 5, column 8, line 68, change "blood stream observing" to --blood stream flow observing--.

Claim 5, column 9, line 25, change "the" to --thereof--.

Claim 7, column 10, line 15, change "reference signal" to --reference frequency signal--.

Claim 7, column 10, line 18, change "and corresponding" to --and producing said data corresponding--.

Signed and Sealed this

Ninth Day of October, 1990

*Attest:*

HARRY F. MANBECK, JR.

*Attesting Officer*     *Commissioner of Patents and Trademarks*